US009448155B2

(12) United States Patent
Pan

(10) Patent No.: US 9,448,155 B2
(45) Date of Patent: Sep. 20, 2016

(54) SYSTEM FOR SAMPLING AND/OR ANALYSIS OF PARTICLES IN A GASEOUS ENVIRONMENT

(71) Applicant: U.S. Army Research Laboratory ATTN: RDRL-LOC-I, Adelphi, MD (US)

(72) Inventor: Yongle Pan, Ellicott City, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/740,676

(22) Filed: Jun. 16, 2015

(65) Prior Publication Data

US 2015/0377764 A1 Dec. 31, 2015

Related U.S. Application Data

(60) Provisional application No. 61/998,366, filed on Jun. 25, 2014.

(51) Int. Cl.

*G01N 1/00* (2006.01)
*G01N 15/14* (2006.01)
*G01N 21/65* (2006.01)
*G01N 15/00* (2006.01)

(52) U.S. Cl.

CPC ...... *G01N 15/1434* (2013.01); *G01N 15/1463* (2013.01); *G01N 21/65* (2013.01); *G01N 2015/0065* (2013.01)

(58) Field of Classification Search

CPC ............... G01N 1/2813; G01N 1/286; G01N 2001/284; G01N 1/2806; G02B 21/32
USPC .......................................................... 356/36
See application file for complete search history.

(56) References Cited

U.S. PATENT DOCUMENTS

| | | | | |
|---|---|---|---|---|
| 5,950,646 | A * | 9/1999 | Horie | B08B 9/00 134/102.1 |
| 2002/0124553 | A1 * | 9/2002 | Lucas | F01N 3/037 60/278 |
| 2004/0255779 | A1 * | 12/2004 | Trivett | B01D 47/06 95/226 |
| 2014/0004559 | A1 | 1/2014 | Hill et al. | |

OTHER PUBLICATIONS

M. Lewittes, S. Arnold, and G. Oster, "Radiometric levitation of micron sized spheres," Appl. Phys. Lett. 40, 455-457 (1982).

(Continued)

*Primary Examiner* — Tarifur Chowdhury
*Assistant Examiner* — MD M Rahman
(74) *Attorney, Agent, or Firm* — Eric Brett Compton

(57) ABSTRACT

A system for trapping particles in a gas comprising a chamber; an intake for intake of a gas containing at least one particle to be trapped and released, and an outlet for exit of the gas out of the chamber containing at least one particle; a first passage operatively connected to the intake operating to create a flow of a gas containing at least one particle into the chamber, a second passage operatively connected to the outlet for flow of the gas; a third passage operatively connected to a gaseous flow for creating a flow of fluid in a direction substantially opposite to the transfer of gas from the first passage so as to counteract the flow of gas from the first passage; an image sensor for recording an image; and a laser for generating a light beam for forming a photophoretic trap between the first and third passages.

20 Claims, 9 Drawing Sheets

(56) References Cited

OTHER PUBLICATIONS

V. G. Shvedov, A. S. Desyatnikov, A. V. Rode, W. Krolikowski, and Yu. S. Kivshar, "Optical guiding of absorbing nanoclusters in air," Opt. Express 17, 5743-5757 (2009).

A. S. Desyatnikov, V. Shvedov, A. Rode, W. Krolikowski, and Yu.S. Kivshar, "Photo-phoretic manipulation of absorbing aerosol particles with vortex beams: theory versus experiment," Opt. Express 17, 8201-8211 (2009).

V. G. Shvedov, C. Hnatovsky, A. V. Rode, and W. Krolikowski, "Robust trapping and manipulation of airborne particles with a bottle beam," Opt. Express 19, 17350-17356 (2011).

P. Zhang, Z. Zhang, J. Prakesh, S. Huang, D. Hernandez, M. Salazar, D.N. Christodoulides and Z. Chen, "Trapping and transporting aerosols with a single optical bottle beam generated by moire techniques," Opt. Lett. 36, 1491-1493 (2011).

Y. L. Pan, S. C. Hill, and M. Coleman, "Photophoretic trapping of absorbing particles in air and measurement of their single-particle Raman spectra," Optics Express, 20 (5), 5275-5334 (2012).

Y. L. Pan, C. Wang, S. C. Hill, M. Coleman, L. A. Beresnev, and J. L. Santarpia, "Trapping of individual airborne absorbing particles using a counterflow nozzle and photophoretic trap for continuous sampling and analysis," Applied Physics Letters 104, 113507 (2014).

* cited by examiner

Trapping Region

SYSTEM FOR SAMPLING AND/OR ANALYSIS OF PARTICLES IN A GASEOUS ENVIRONMENT

CROSS REFERENCE TO RELATED APPLICATION(S)

This application claims the benefit of U.S. Provisional Patent Application No. 61/998,366 filed Jun. 25, 2014, herein incorporated by reference in its entirety for all purposes.

STATEMENT OF GOVERNMENT INTEREST

The invention described herein may be manufactured, used, and licensed by or for the United States Government without the payment of royalities. It resulted at least in part from research supported by the U.S. Army Research Laboratory (ARL) funds and by the Defense Threat Reduction Agency (DTRA) under contract number HDTRA136477, US Army Research Office grants W911NF-13-1-0429 and W911NF-13-1-0297.

BACKGROUND OF THE INVENTION

Measurements of single particles trapped in air have been made since the pioneering work on electro-quasistatic levitation (Fletcher, H., "A Determination of Avogadro's Constant N from Measurements of the Brownian Movements of Small Oil Drops Suspended In Air," Phys. Rev. 4, 440-453 (1914) and optical levitation (Ashkin, A., "Acceleration and Trapping of Particles by Radiation Pressure," Phys. Rev. Lett. 24, 156-159 (1970). These techniques have been used to measure single-particle Raman spectra. The power of such Raman measurements is clearly recognized. However, the one reported attempt to measure single-particle Raman spectra of atmospheric aerosols achieved such a low sample rate that the authors wrote that the measurements were "tedious." A problem in that approach is that charging of the aerosols was required. Only a fraction of the particles have the needed charge-to-mass ratio to be captured. Optical trapping using radiation pressure is useful for "suspending relatively transparent particles in relatively transparent media," but it has not been used to sample and trap successively arriving particles from atmospheric air.

Previous attempts have been made using methods and/or systems for particle trapping using photophoretic force. However, the previous methods for trapping particles in air are generally capture and trap one single particle from a large group of particles (e.g., a few to 1000's) passively (a particle is randomly trapped). Furthermore, in those methods, these particles are initially placed on a substrate or in a container and then forced into the air in a short time to generate very high particle concentrations for trapping. Such passive particle trapping approaches have low efficiency, are not suitable for continuously sampling and trapping.

The existing on-line analytical systems (e.g. single-particle fluorescence spectrometer, mass spectrometer) generally concentrate and focus the aerosol into a localized jet, and then the particles flows into an interrogation region carried by the airflow, where the particles are analyzed one-by-one as they rapidly flow through (they are not trapped in stationary at any location). The flowing through systems cannot be used for the measurement that has very weak signal such as Raman scattering signal, and also cannot be used for observing time-revolution process.

The existing optical trapping techniques used to study the physical, chemical, or biological properties of one or a few representative particles in air generally capture and trap the particles from a large group of particles (e.g., a few to 1000's). The particles to be trapped typically have to be with similar properties and are initially placed on a substrate or in a container and then forced into the air in a short time to generate very high particle concentrations for trapping. Such low efficiency, passive particle trapping approaches are not adequate for continuously sampling and trapping for the successively arriving particles with different properties.

The prior art technology includes methods and apparatus where particles are randomly captured and/or trapped; such as when particles are spread out and randomly captured by entering a trap zone. Such processes are time-consuming and require the source of particles to be physically and chemically uniform; otherwise the trapped particles may not be representative of typical ones (due to the feature of randomization of the methods). This problem hinders instrumentation for continuously sampling and trapping aerosol particles that arrive successively in the trapping system from an air stream that likely have particles in different physical and chemical properties.

SUMMARY OF THE INVENTION

The present invention overcomes the above problems, as it affords the opportunity to capture and trap particles that have different properties. Particles may be continuously sampled and successively fed into the trapping region, held for observation and measured as long as needed. The present invention improves the particle trapping rate from the existed passive capturing methods. The present invention provides the optional capabilities of concentrating particles from air (or a gas), focusing these aerosol particles into a narrow jet, slowing the particles, trapping the particle in a region where the particle velocity has become very small, retaining the particle for as long as needed, and releasing the trapped particle in order to trap the next one. The present invention allows one to continuously sample successively arriving aerosol particles and suspend them for measurements.

Figure 1A:
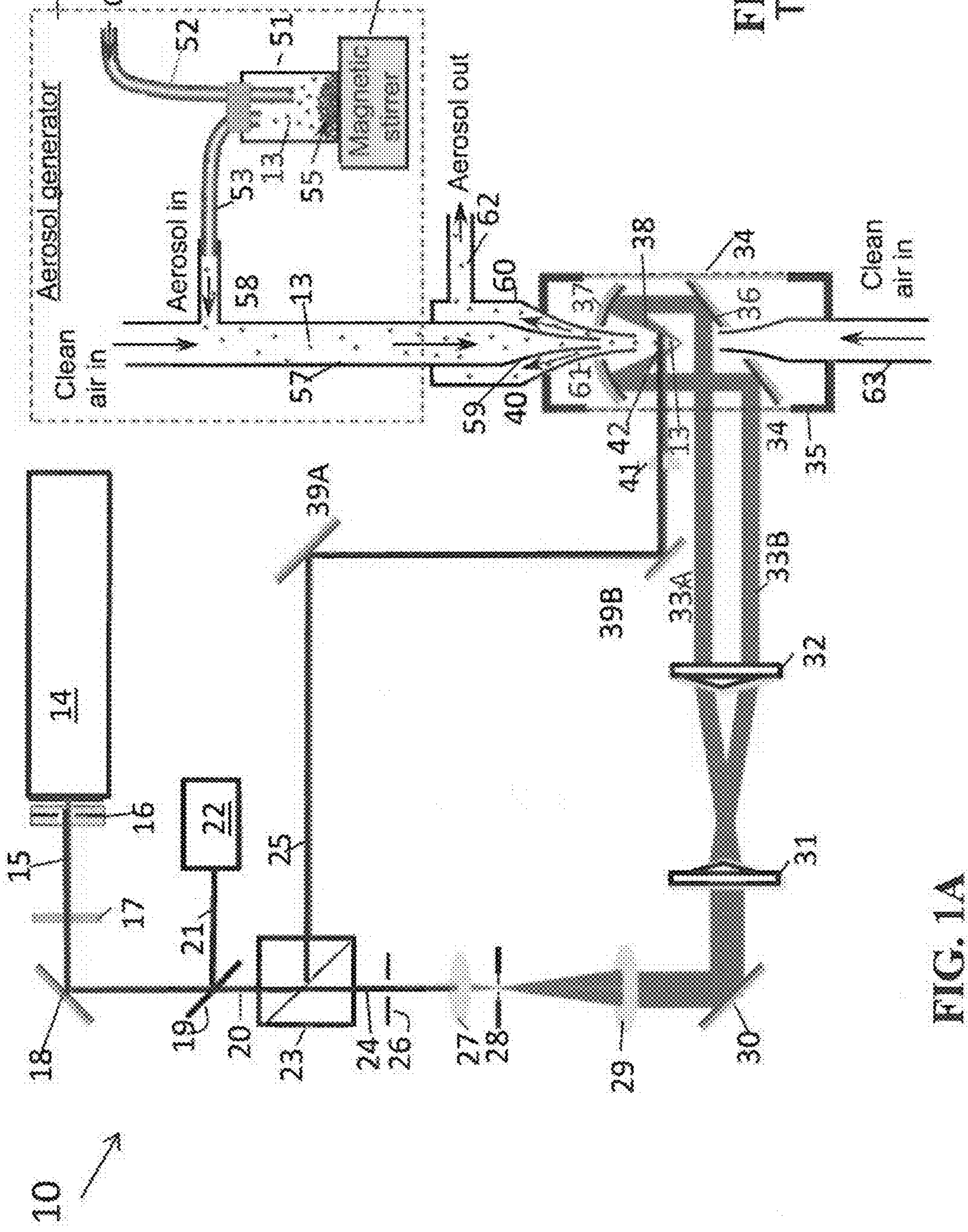
FIG. 1A is a schematic illustration of a preferred embodiment of the present invention.

The foregoing and other objects, features, and advantages of the invention will be apparent from the following more detailed description of the preferred embodiments of the invention, as illustrated in the accompanying drawings, wherein:

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximates.

DESCRIPTION OF THE PREFERRED EMBODIMENTS

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention. Rather, these embodiments are provided so that this disclosure will be thorough and complete, and will fully convey the scope of the invention to those skilled in the art. In the drawings, the dimensions of objects and regions may be exaggerated for clarity. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element such as an object, layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It will be understood that, although the terms first, second, etc. may be used herein to describe various elements, components, regions, layers and/or sections, these elements, components, regions, layers and/or sections should not be limited by these terms. For example, when referring first and second passages, these terms are only used to distinguish one passage, element, component, region, layer or section from another passage, region, layer or section. Thus, a first passage, element, component, region, layer or section discussed below could be termed a second passage, element, component, region, layer or section without departing from the teachings of the present invention.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in the Figures is turned over, elements described as being on the "lower" side of other elements would then be oriented on "upper" sides of the other elements. The exemplary term "lower", can therefore, encompass both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below. Furthermore, the term "outer" may be used to refer to a surface and/or layer that is farthest away from a substrate.

Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes. Thus, the regions illustrated in the figures or configurations are schematic in nature and their shapes are not intended to illustrate the precise shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will also be appreciated by those of skill in the art that references to a structure or feature that is disposed "adjacent" another feature may have portions that overlap or underlie the adjacent feature.

A preferred embodiment design able to focus, concentrate, and also make these particles move slowly to be trapped in air from successive arriving airborne aerosol particles that are continuously sampled from air. The invention provides feeding methods for trapping particles in air, and is very useful in various on-line analytical applications, in which long-time monitoring or analyzing from a series of successive arriving particles (e.g. different kind of individual particles from atmosphere, pharmaceutical or other production facilities) is required, as the invention permits each particle to be trapped for a short time (e.g. a few seconds) for observation or measurement. The present invention provides a new method for continuous sampling, trapping, holding, and releasing aerosol particles in air in an effective way that the entire process is actively controlled. A preferred embodiment comprises, inter alia, two components: 1) a laser and optics formed hollow cone surrounded by a conical high-intensity light surface that can trap absorbing particles carried into the cone by an air or gaseous stream. 2) two passages, which may be in the form of two co-axial nozzles operated in a counter flow mode, so that: i) particles are aerodynamically focused and concentrated into a small-diameter jet; and ii) particles are slowed such that velocity of the particles approaches zero near the vertex of a hollow optical cone, so that particles move slowly enough to be trapped by photophoretic forces that are able to balance the small drag and gravitational forces.

A preferred embodiment of the present invention may be utilized as an online instrument for detecting and characterizing aerosols, particularly as a real-time device for detecting aerosolized biological, chemical threats using more informative optical signatures such as Raman spectra with a significant reduction of false positive alarm rate. The present invention provides the capability of on-site instrument for air quality characterization and monitoring, such as in a battlefield situation. The present invention further provides for long-time monitoring or analyzing from a series of successively arriving particles (e.g. different kind of individual particles from atmosphere, pharmaceutical or other production facilities) by trapping the particles for a short time (e.g. 1 to a few seconds) for observation or measurement.

Potential commercial uses include: (1) On-line aerosol characterization instrumentation; (2) On-line material characterization (3) Pharmaceutical usage for drug testing and delivery (4) Single aerosol particle spectroscopic sampler.

A preferred embodiment system of the present invention comprises an integrated opto-aerodynamic system that can repeatedly sample, trap, and release airborne micron-size aerosol particles. The particles may be concentrated from as gas, such as air, for example, which transports them into a narrow jet. The jet is then slowed along with particles in it, in order to trap one or more absorbing or weakly-absorbing particles in a region where the jet velocity has become very small, The particle may then be held for as long as needed, and released in order to trap the next one. The system can utilize in conjunction with an on-line analytical system that provides for continuous sampling of successively arriving aerosol particles and holding the particles for measurements and time-related phenomena.

FIG. 1A is a schematic illustration of a preferred embodiment 10 of the present invention for sampling, trapping, and releasing airborne micron-size aerosol particles for on-line observation or measurement. In the exploded view of FIG. 1B, the photophoretic trapping region is formed by a hollow conical beam 38 which can be covered by a laser sheet 42 once a particle 13 is trapped, in order to prevent additional particles from entering the trap. Particles 13 are aerodynamically focused and concentrated into a localized jet by the inner nozzle and slowed by a counter flow of air surrounding the jet from the outer nozzle and moves particles into the trapping region very slowly.

Figure 1B:
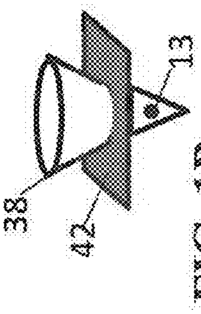
FIG. 1B is an exploded view of the trapping region.

FIG. 1A illustrates the arrangement of preferred embodiment 10. The trapping light source 14 may be, for example, a continuous-wave argon ion laser at 488 nm (Lexel Laser, 95-SHG) or other laser source at different wavelengths. The light source 14 produces a linearly polarized Gaussian beam 15. The output power may be adjustable, such as by changing the plasma tube current and/or the neutral density filters 17. The laser beam 15 from light source 14 may be controlled by shutter 16. As a further option, mirror 18 reflects the laser beam into a non-polarized beam splitter 19 which separates the beam into two beams 20, 21, one of which (21) enters a power meter 22 for monitoring the laser power. The main beam 20 enters a beam splitter 23 (which may be a 50/50 beam splitter) which divides the beam into beams 24, 25, the first of which forms the cone portion of the photophoretic trap and the second of which (25) forms the laser plate portion of the photophoretic trap. Beam 24 is formed into a conical trapping region surrounded by a high-intensity-light at the surface of the cone. The laser beam 24 forming the cone portion 38 of the photophoretic trap is cleaned by an iris 26, a 500-pmn-diameter pinhole 28 and re-collimated using two lenses 27, 29 (f=25 mm and 180 mm). The expanded (approximately 15 mm in diameter) collimated beam is transformed into a hollow beam (doughnut-shaped transverse intensity profile) by passing it through two axicons 31, 32 separated by 50 cm (Del Mar Photonics, cone angle 175°). As shown in FIG. 1A, beam 24 passes through a first lens 27 and is reflected by a mirror 30 into axicon lenses 31, 32 which produce beams which are reflected by an elliptical mirror 36. The re-collimated hollow beam (shown in cross section by lines 33A, 33B) is approximately 20 mm in diameter with a low-light-intensity center (~7 mm in diameter). FIG. 1A shows the 2-dimensional cross section of the laser beam along its axis, so the hollow beam is indicated by two broad lines 33A, 33B. The hollow beam, introduced through a quartz window 34 into an air-tight chamber 35, is reflected by the elliptical mirror 36 at 45°, propagates up to a concave spherical mirror 37 (f=19 mm, diameter=25.4 mm), and reflects from it to form the low-light-intensity conical region 38 surrounded by the high-intensity-light at the surface of the cone. The high-intensity-light is focused to a spot approximately 5 mm below the tip of the outer nozzle (counter-flow nozzle). FIG. 1B labeled "trapping region" illustrates this region in a three dimensional image. Each mirror inside the chamber 35 has a center hole 40 to let the aerosol or air flows pass through. The four sides of the chamber 35 are covered by quartz windows 34 to provide a large solid angle (>0.3π for each side) for observation.

Referring back to the beam splitter 23, the other beam 25 is reflected by optional mirrors 39A, 39B onto a cylindric lens 41 to form a laser sheet 42 to cover the cone as a high-intensity light wall on the open side of the hollow cone.

It can hold the captured particle and also prevents other absorbing particles from entering the trapping region by photophoretic forces.

Parts in the integrated opto-aerodynamic embodiment illustrated in FIG. 1A include the counter-flow co-axial double-nozzle 59, 61, the optical chamber 35, the reflecting elliptical mirror 36, and the focusing spherical mirror 37.

In FIG. 1A, one of the methods for generating aerosol 50 is also shown. One of ordinary skill in the art would appreciate that in the case where the particles are in the air, generating aerosol particles would be unnecessary. When used in an experimental environment, the aerosol generator 50 comprises a container 51 containing the particles to be analyzed. Air is inputted through a hose or tubing 52 and outputted through a hose or tubing 53. A magnetic stirrer 54 operating in conjunction with a magnetic bar 55 stirs the particles/powder at a sufficient rate to generate the aerosol particles 13. Aerosol particles 13 pass through outlet tubing or hose 53 into a pipette-like structure 57 have a side inlet 58 through which the aerosol enters and a top opening though which the clean air enters. The particles 13 pass downwards through a narrow region or nozzle or inlet 59 of the cylinder or pipette 57. A second chamber 60 having a narrowed outlet portion or nozzle 61 surrounds the nozzle or inlet portion 59. Aerosol particles 13 pass through the narrow inlet passage or nozzle 59 to the trapping region as explained above and shown in FIG. 1B. Specifically, the two co-axial nozzles 59, 61 (inlet and outlet passages, respectively) are operated in a counter flow mode so that particles 13 are aerodynamically focused and concentrated into a small-diameter jet; and the particles 13 are slowed (by a counter flow of air from nozzle 63 which slows the jet in which they are entrained) until their vertical velocity approaches zero near the vertex of the hollow optical cone, so that particles 13 move slowly enough to be trapped by photophoretic forces that are able to balance the small drag and gravitational forces. The particles 13 can return via the outer coaxial nozzle 61 into the second chamber 60 to be exhausted via the outlet 62 if they are not trapped or released after trapping. At the same time clean air is provided though a third nozzle 63 so as to provide a small portion of the counter flow referenced above.

Figure 1C:
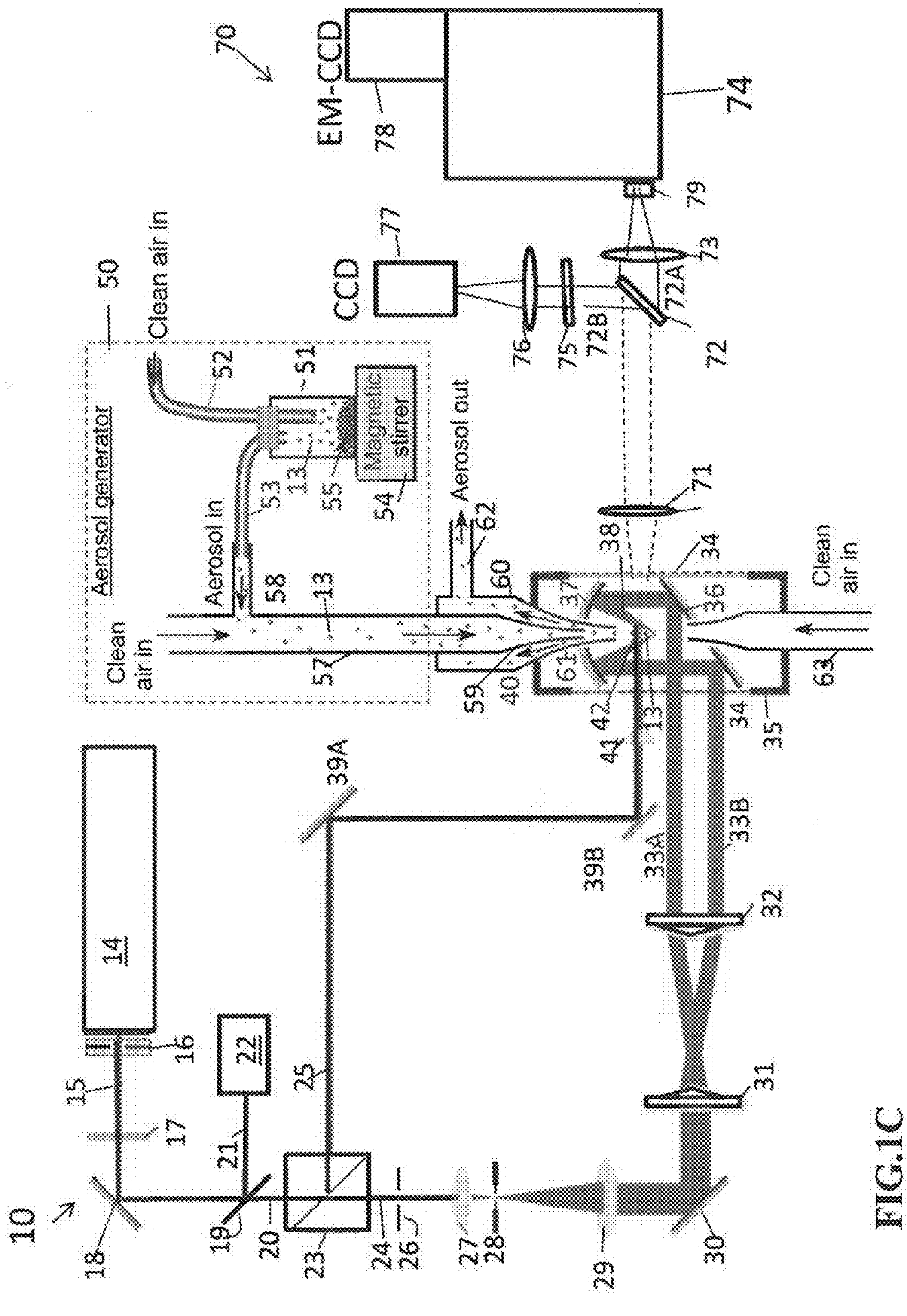
FIG. 1C is a schematic illustration of the preferred embodiment of FIG. 1A with an optional spectrograph and detector subassembly 70.

FIG. 1C is a schematic illustration of the preferred embodiment of FIG. 1A with an optional spectrograph subassembly 70. All of the components relating to the preferred embodiment 10 of FIG. 1A are incorporated herein by reference as though fully recited herein. In addition, elastic and inelastic scattering light 72 from the particle being collected by a lens 71 is separated by a dichroic beam splitter (DBS) 72 where it is split into beams 72A and 72B. Light beam 72A passes through lens 73 into spectrograph 74 (e.g., via a long pass filter 79). Light beam 72B passes through neutral density (ND) filter 75 and through lens 76 and images into CCD 77. CCD 78 records the image or spectrum dispersed by the spectrograph. The inelastic signal could be fluorescence, Raman scattering signal or others. Charged coupled devices 77, 78 could be other image sensors such as cameras or the like.

Figure 2:
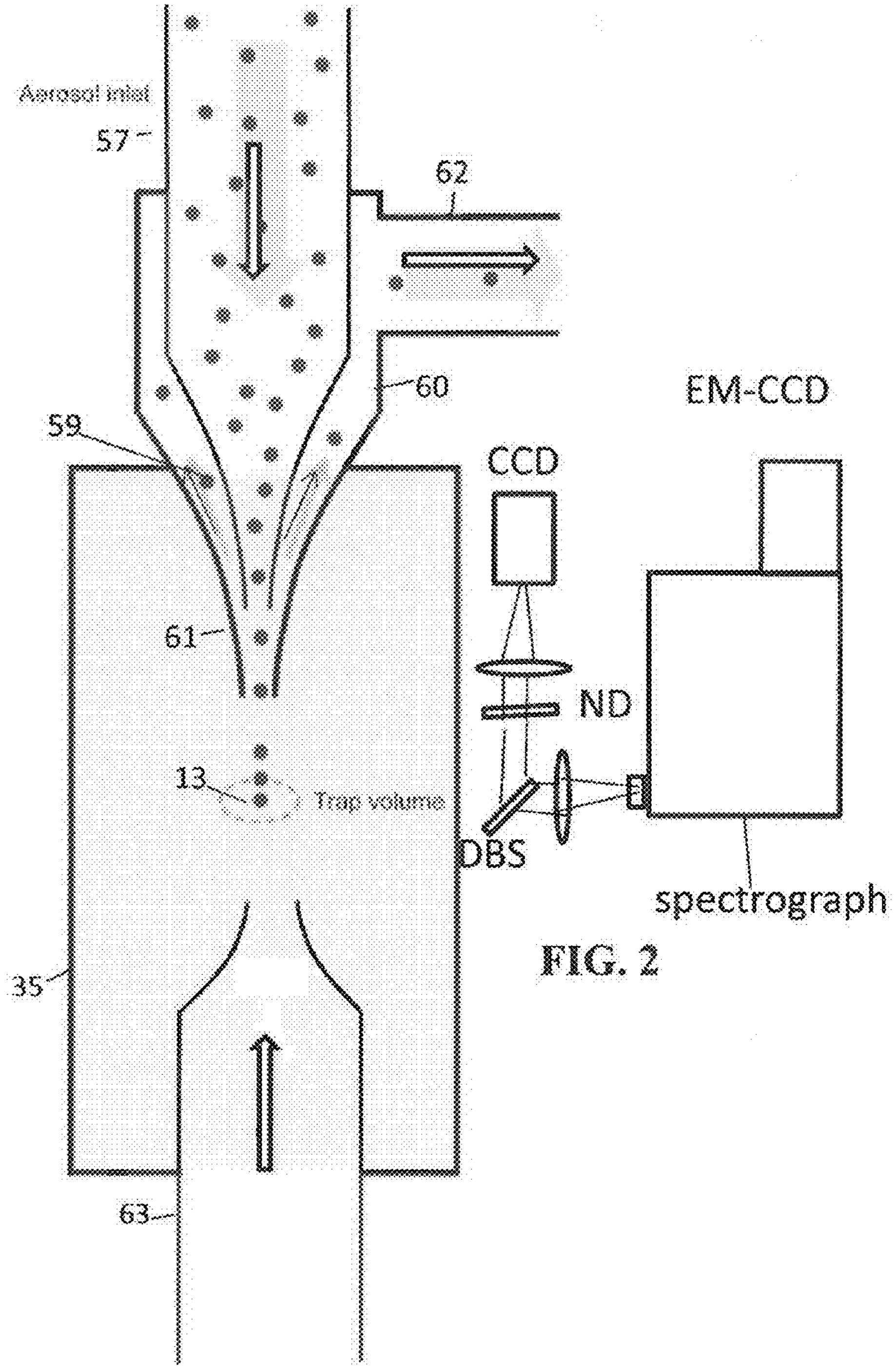
FIG. 2 is a schematic illustration of a portion of a preferred embodiment showing, inter alia, the aerosol flow (as seen by arrows) from first passage (or coaxial nozzle 59) into chamber 35, clean air flow from the passage or nozzle 63 into chamber 35, and the exiting of aerosol flow through the second passage between nozzles 59, 61 into chamber 60 and out through outlet 62.

FIG. 2 is a close-up schematic illustration of flow of air and aerosol particles from the passages into the chamber 35 of the preferred embodiment of FIG. 1A, showing, inter alia, the air flow (as seen by arrows) from nozzle or passage 59 into chamber 35 and exiting through the passage between nozzles 59, 61 in chamber 60 and out through outlet 62. Also shown is the counter balancing flow from the third passage or nozzle 63 into chamber 35.

Utilizing the preferred embodiment of FIGS. 1A and 2, aerosol particles are continuously sampled into the inner nozzle 59, then aerodynamically focused and concentrated into a small-diameter jet within 300 μm diameter by the carrying airflow. After exiting the first passage (or inner nozzle 59), the airflow is pulling in a reverse direction in the outer passage of coaxial-nozzle 61, while the air speed decreases, the particles are also slowed by the drag forces resulting from the particle's inertia tending to remain constant, i.e., to keep the particle velocity greater than that of the airflow. Eventually the downward component of the air velocity and the particle velocity decreases to zero and changes and turn 180°. The particles and the air then move laterally out of the jet and into the counter flowing air stream which is drawn back up into the outer passage or nozzle 61, and they exit through the outer nozzle. The trapping region is set a little above the center of zero-velocity point. This design reduces the downward Stokes drag force on the particle in the region where the particle is trapped so that a photophoretic force is strong enough to stop the particles and trap them. The small drag from the downward airflow along the central line, the gravitational force and optical (mostly photophoretic) forces push the particle to the point where it is trapped. Particles that touch the high-intensity-light surface of the confining cone will be pushed toward the axis of the aerosol jet by the photophoretic forces and pushed towards the focal point by optical pressure forces, which for absorbing particles are typically small compared to the photophoretic forces, pulled down toward the vertex of the cone with gravity. The combination of the designs (optical trapping cone and counter-flow coaxial-double-nozzle) makes it possible to readily capture and trap particles continuously drawn into the chamber.

The preferred embodiment system of FIG. 1A can repeatedly capture a particle from a jet of micron-size aerosol particles that are continuously drawn into the chamber, and then trap the particle for measurement or observation, and release it (by blocking and unblocking the trapping laser beam). In a test experiment, the trapping laser power is 50 mW. The particles shown are aggregates (approximately 20-μm average diameter with large variance) of multi-walled carbon nanotubes (MWCNTs) which have an outside diameter less than 7 nm, an inside diameter approximately 2-5 nm, and a length approximately 10-30 μm. During a one minute time period, more than 10 particles have been captured, trapped, and released. A new particle can be captured and trapped from a jet within one second, once the laser is unblocked. The trapping rate could be increased by reducing the time that the particle is in trap and the time the laser is blocked. The preferred embodiment of FIG. 1A can repeatedly sample, trap, and release light-absorbing airborne micron-sized aerosol particles that are continuously drawn into a chamber. This technology has the potential to be developed into a new analytical instrument for on-line observation or measurement.

Figure 3:
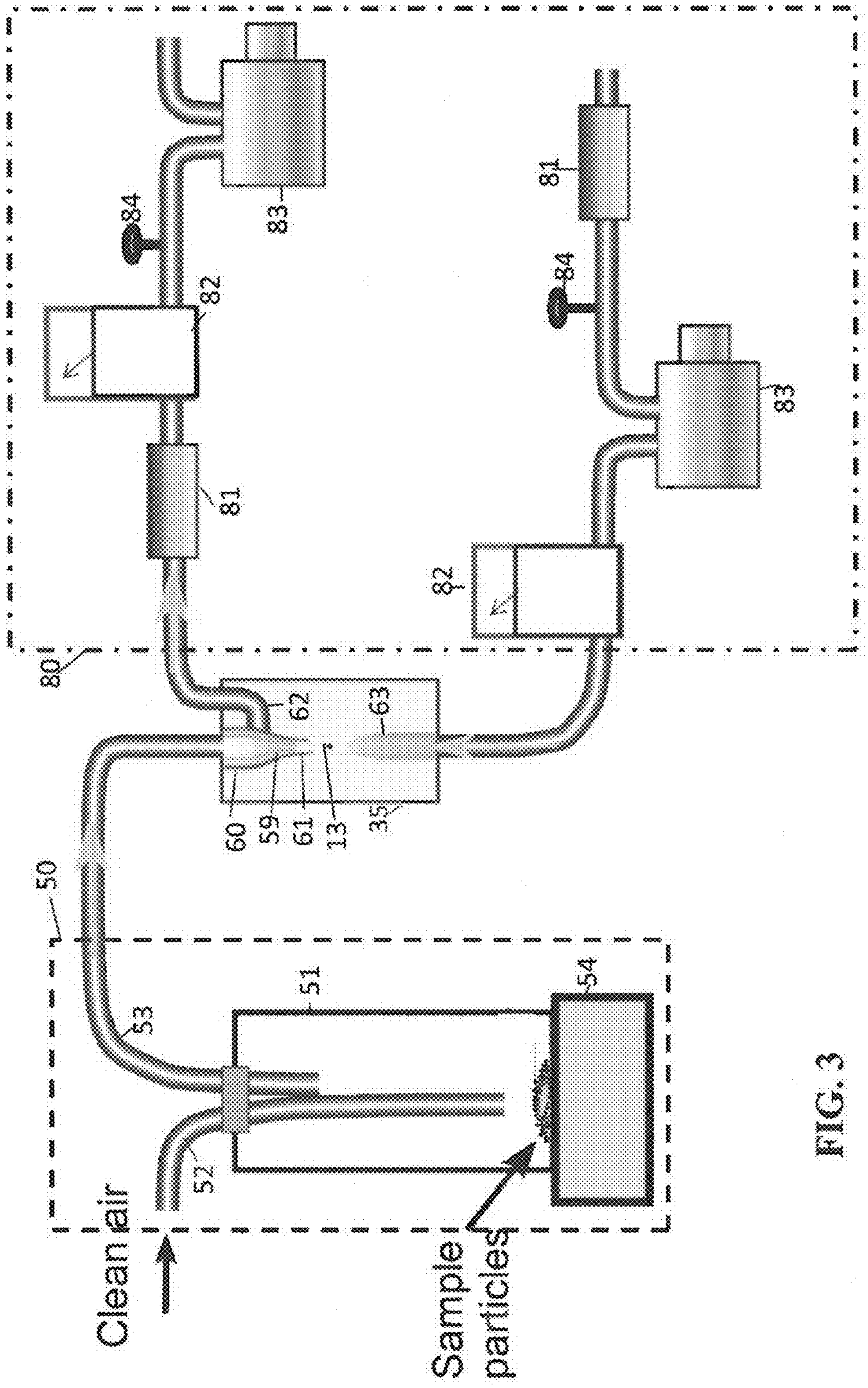
FIG. 3 is a schematic illustration of the optional gas flow portion of a preferred embodiment.

FIG. 3 is an example schematic drawing of the aerodynamic design showing optional additional flow generating, monitoring and filtering subassembly 80. The embodiment of FIG. 3, set forth in diagrammatic form, is intended to include all the elements of the preferred embodiment 10 illustrated in FIG. 1A, which are herein incorporated by reference as though pictured and fully rewritten herein; and in addition, include an optional subassembly 80. Subassembly 80 may optionally be divided into two sections (such an input and exhaust) or more than two sections.

As shown in FIG. 3, subassembly 80 includes filters 81, flow meters 82, pumps 83, and valves 84, not necessarily arranged in the order shown in FIG. 3. The preferred methodology of FIG. 3 is as follow:

1. Sample aerosol at 1 L/min to get sufficient sampling rate and match that of most concentrators (e.g. MSP, XMX).
2. Focus particles to a small stream to deliver more particles to the small trap volume.
3. Slow particles by the counterflow from nozzle 63.

To achieve sampling particles from air at a reasonable rates (e.g., approximately 1 liter/second), while retaining the ability to capture and study the particles, the following techniques are applied.

(1) "Gating on" or the Trapping Beam as the Particle Enters the Trapping Region.

Particles are detected by measuring the elastic scattering as the particles approach the trapping region, so that the trapping laser beam is "gated on" or unblocked at the correct time to trap the particle. Particularly beam sheet 25 "turn on" to prevent other particles into the trapping volume and further solid the trap when a particles is trapped. Once the measurement is finished, the trapping beam is unblocked to let the particle be carried away in the airstream. Once the trapping beam is "on", the high intensity light surface of the cone and the sheet will prevent any other particles entering the trapping region (i.e., inside the cone region). The beam 24 can keep on all the time, and only "off" for release the trapped particle when a measurement or observation is finished for it.

(2) Selection of the Most Suitable Laser Wavelengths for Trapping and Illumination.

Because most biological and chemical particles absorb light strongly in the 220 to 245-nm range, and fluoresce at wavelengths longer than 280 nm, a short-wavelength laser (220 to 245 nm range) is used for both trapping particles and exciting Raman. The Raman signals generated will be increased as $(1/\text{wavelength})^4$, and enhanced by the near-resonance excitation. Also, the Raman spectra will be separated from the fluorescence, which can otherwise interfere. If an illumination laser wavelength in the non-absorbing region is needed for other studies, a beam from a laser with different emission wavelength can be introduced. If desired, it can be tightly focused to the position of the trapped particle. If so, the radiation pressure force generated by this second laser could add an additional trapping force to push the particle towards the position of highest laser intensity, but might also push other particles to the trapping region.

(3) Utilization of Virtual Impaction to Increase the Sampling Rate by Concentrating the Particles while Also Slowing the Particles to Maintain the Trapping Efficiency.

Sampling aerosol at 1 L/min through a 1 mm diameter nozzle causes the particles to move at approximately 10 m/sec. To concentrate particles, a nozzle is used, but most of the airflow is drawn in a direction perpendicular to the aerosol stream; while drawing a minority flow containing the concentrated particles on a straight path as they leave the nozzle. Then the velocity of the minority flow will be reduced to 1 m/sec or less. The reduced particle momenta will be low enough for the photophoretic forces to trap the particles.

Figure 4B:
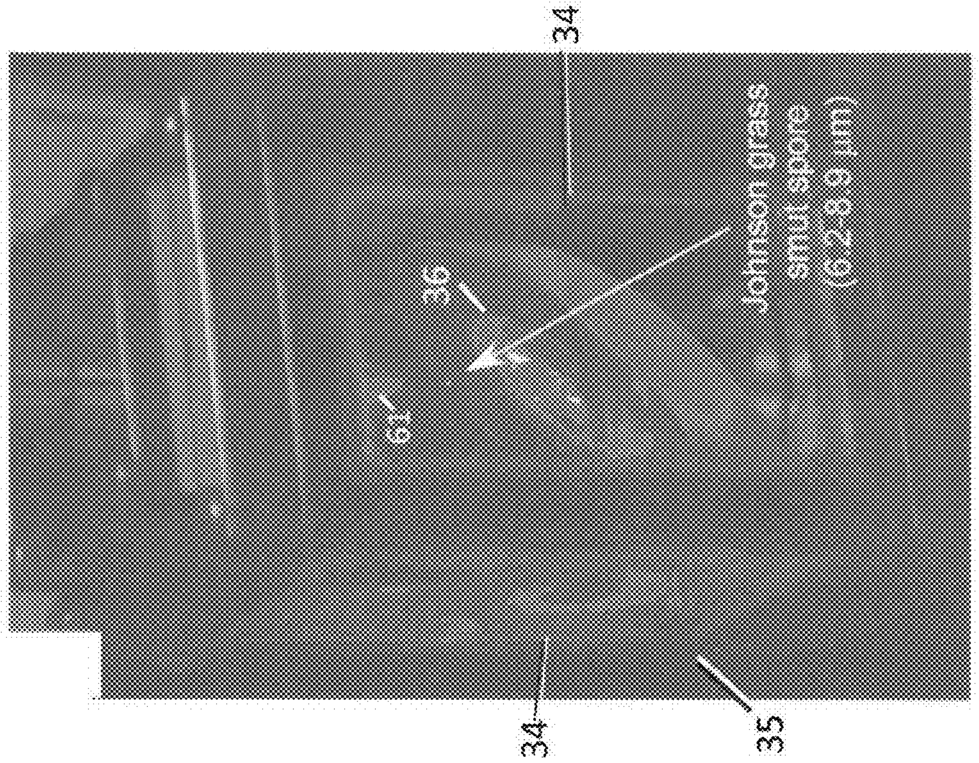
FIG. 4B is a photographic illustration of the chamber 35 shown in FIG. 4A showing operation of a preferred embodiment in conjunction with a Johnson Grass Smut spore (approximately 6.2-8.9 μm).
Figure 4A:
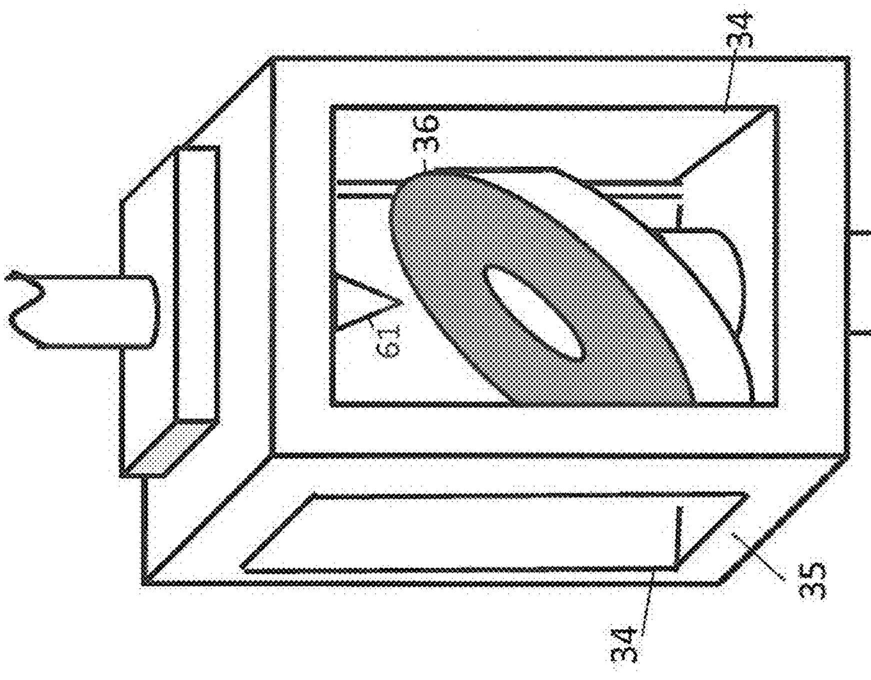
FIG. 4A is a schematic illustration of a chamber 35 having four transparent quartz windows 34.

FIG. 4A is a schematic illustration of a chamber 35 having four transparent quartz windows 34.

Figure 4C:
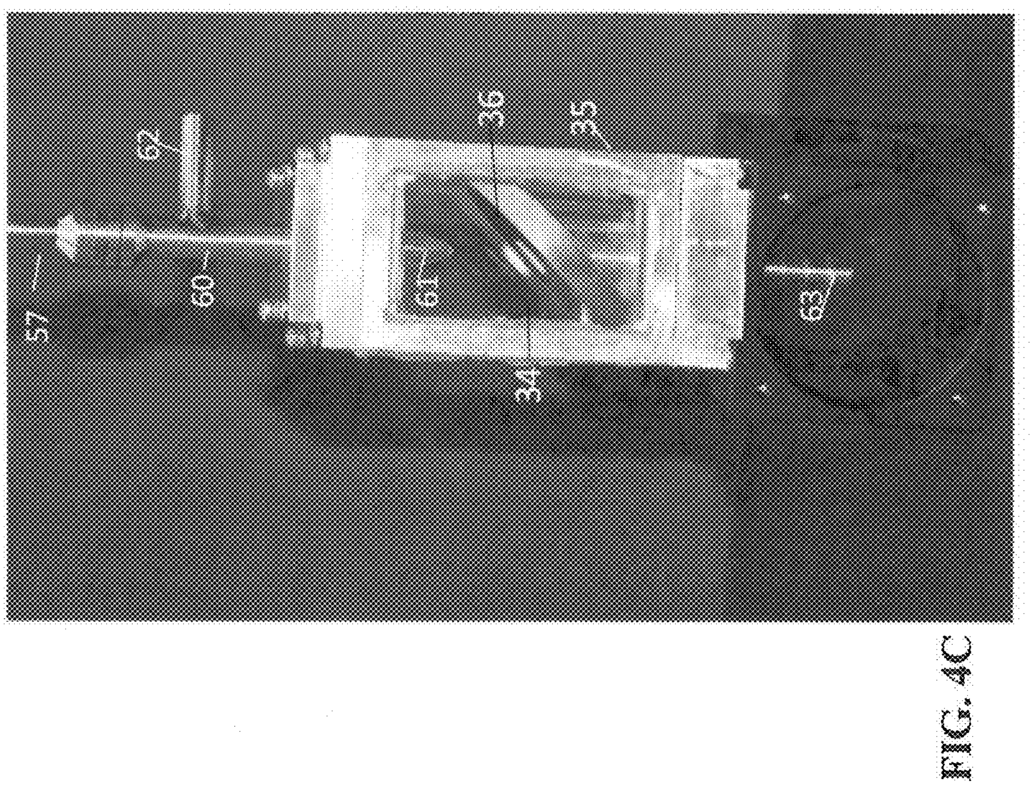
FIG. 4C is another photographic illustration from a different camera angle of the chamber 35 shown in FIG. 4A.

FIG. 4B, 4C is a photographic illustration of the chamber 35 shown in FIG. 4A showing operation of a preferred embodiment in conjunction with a Johnson Grass Smut spore (approximately 6.2-8.9 μm). For highly absorbing particles, the photophoretic force and drag force (from the very weak downward airflow immediately above the region where the downward flow stops) are the main forces for trapping. For absorbing particles with much weaker absorptivity, radiation pressure forces may also contribute significantly to the trapping forces, pulling the particle toward regions with high optical intensity gradients near the vertex of the cone. Non-absorbing particles tend to be very difficult to capture and trapped with the present experimental conditions.

Figure 5:
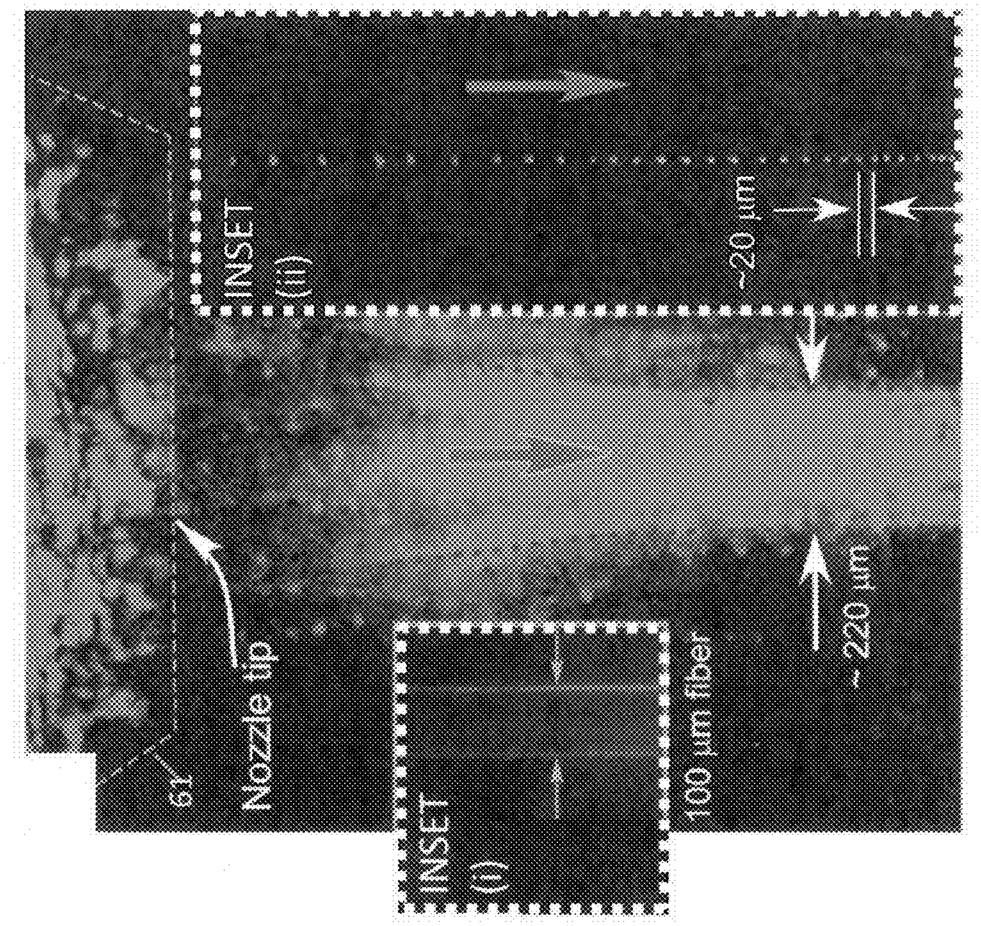
FIG. 5 is a photographic illustration showing flow of a series of particles (shown in inset (ii)) in conjunction with the operation of a preferred embodiment. The system creates an aerosol flow having a diameter of approximately 220 μm.

FIG. 5 is a photographic illustration showing operation of a preferred embodiment in conjunction with inset (i) 100 μm diameter fiber (for a rough scale comparison factor) and inset (ii) a series of particles. The nozzle tip creates a flow having a width of approximately 220 μm. FIG. 5 is a 5 second-exposure image (recorded with a CCD) from the moving trajectories of about 50 tryptophan particles (average diameter 8 μm) recorded by a CCD. Particles are visualized by the illumination of a pulsed 527-nm laser sheet at 1 KHz. Most of the particles are focused into an aerosol jet which has 220-μm diameter at approximately 1.5 mm below the outer nozzle tip. Inset (ii) is the trajectory of a typical trajectory of a moving particle moving within 1.5 mm below the outer nozzle tip. It is slowed from 80 mm/sec near the top to 20 mm/sec in less than 1.5 mm. The bright spots are from the light scattered by the particle at the position when it is illuminated by the pulsed laser. Each millisecond (ms) the particle moves from one spot to the next. Therefore, the speed of the moving particle can be estimated to be the distance between two adjacent spots divided by 1 ms. In this illustration the particle slowed from about 80 mm/sec to 20 mm/sec in approximately 23 ms and in less than 1.5 mm. FIG. 5 illustrates how rapidly the particles are slowed. Typically in concentrating and focusing particles for air sampling the air velocities are greater than 1 m/s, often 20 times greater. If a micron-sized particle needed to be trapped in an airflow of 1 m/s, the drag force on the particle would exceed achievable CW optical forces on the particle. Drag would make it extremely difficult, if not impossible, to optically trap particles moving at these speeds. In the embodiments shown in FIGS. 1A, 1C, 2 and 3, the airflow is slowed by introducing an outer coaxial-nozzle 61 (*the* passage between nozzles 59, 61) and pulling the air in a reverse direction from that typically used focusing nozzles. As the air speed decreases, the particles are slowed by the drag forces resulting from the particle's inertia tending to remain constant, i.e., to keep the particle velocity greater than that of the airflow. Eventually the downward component of the air velocity and the particle velocity decreases to zero and changes sign. The particles and the air then move laterally out of the jet and into the counter flowing air stream which is drawn back up into the nozzle, and they exit through the outer nozzle 61. The trapping region is set a little above the center of zero-velocity point. This design reduces the downward Stokes drag force on the particle in the region where the particle is trapped so that a photophoretic force is strong enough to stop the particles and trap them. The small drag from the downward airflow along the central line, the gravitational force and optical (mostly photophoretic) forces push the particle to the point where it is trapped. Particles that touch the high-intensity-light surface (shown as 43 in FIG. 1B) of the confining cone (shown as 38 in FIG. 1B) will be pushed toward the axis of the aerosol jet by the photophoretic forces and pushed towards the focal point by optical pressure forces, which for absorbing particles are typically small compared to the photophoretic forces, pulled down toward the vertex of the cone with gravity. The combination of the designs (optical trapping cone and counter-flow coaxialdouble-nozzle) makes it possible to readily capture and trap particles continuously drawn into the chamber.

Figure 7:
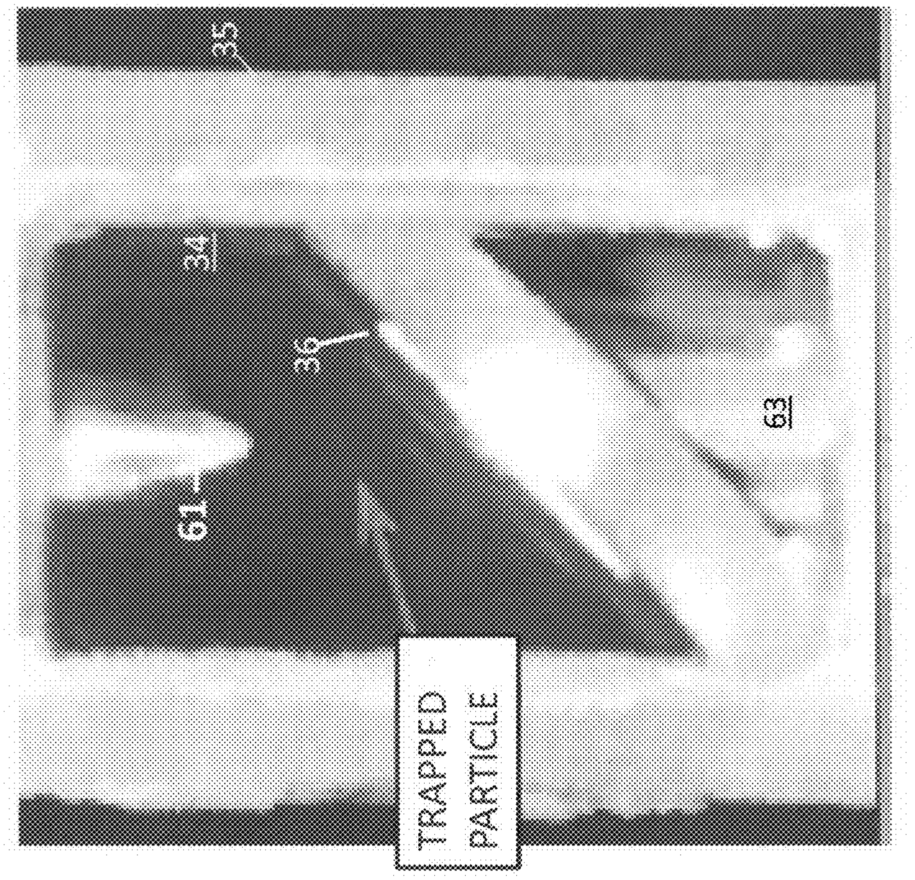
FIG. 7 is a photographic illustration showing a close-up of a particle captured from a jet of micron-size aerosol particles that are continuously drawn into the chamber 35, and then trapped and released by blocking and unblocking the trapping laser beam.
Figure 6:
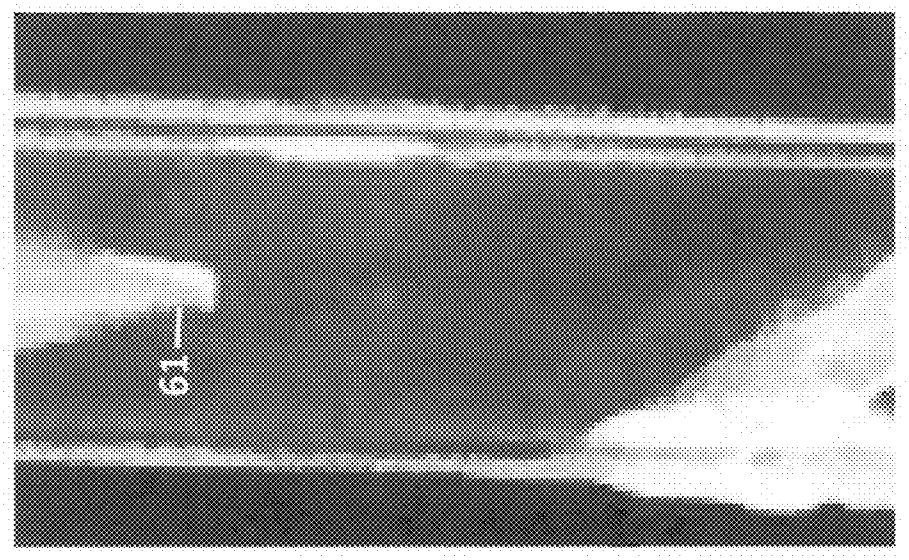
FIG. 6 is a photographic illustration of an alternate embodiment wherein 8-μm diameter tryptophan particles move one by one inside a 1 cm×1 cm quartz cell.
Figure 8:
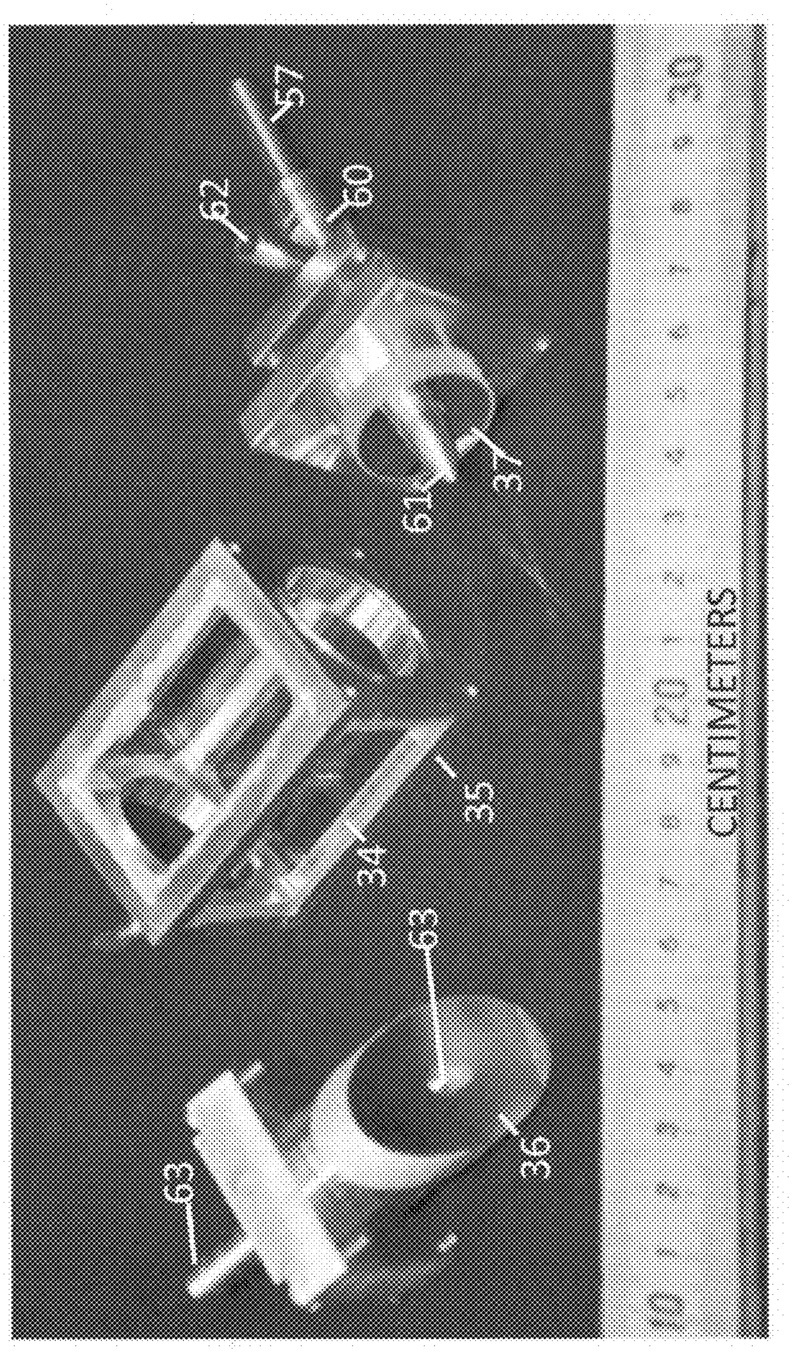
FIG. 8 is a photographic illustration of a preferred embodiment chamber assembly separated in to three components.

FIG. 6 illustrates an alternate embodiment wherein 8-μm diameter tryptophan particles move one by one inside a 1 cm×1 cm quartz cell. In this embodiment there is no optical trapping cone. These particles were also visualized by illuminating with the pulsed 527-nm laser operating at 1 KHz. The particles exit the tip of the outer nozzle 61 at approximately 100 mm/sec, which was already slowed from approximately 2 m/sec exiting the inner nozzle 59. Typically particle moves rapidly until it approaches the turning point about 5 mm below the nozzle. It then moves upwards first slowly and then more quickly. The particles exit the chamber through the outer part of the outer nozzle. FIG. 6 illustrates that super micron particles could be focused into a localized small-diameter jet with a velocity that goes to zero. Such a novel design provides a new technique that can concentrate and focus particles into a localized aerosol jet and then deliver them into a small region at a very low speed (the vertical component of its velocity goes transiently to zero). This coaxial-double-nozzle running in a counter flow mode should be also useful for trapping particles using electrodynamic or ultrasonic forces (rather than optical forces) for continuous sampling. IG. 7 illustrates how the system can repeatedly capture a particle from a jet of micron-size aerosol particles that are continuously drawn into the chamber, and then trap the particle and release it (by blocking and unblocking the trapping laser beam). The trapping laser power is 50 mW. The particles shown are aggregates (approximately 20-μm average diameter with large variance) of multi-walled carbon nanotubes (MWCNTs) which have an outside diameter less than 7 nm, an inside diameter approximately 2-5 nm, and a length approximately 10-30 μm. During a one minute time period, more than 10 particles have been captured, trapped, and released. In the illustration of FIG. 7, a new particle can be captured and trapped from a jet within one second, once the laser is unblocked. The trapping rate could be increased by reducing the time that the particle is in trap and the time the laser is blocked. The trapped particles appear as bright or dim spots (with stronger or weaker scattering intensities), which may be from larger or smaller particles, or from a particle scattering more or less as it trapped a little further or closer to the highest-intensity light of the vertex. When the laser sheet beam is not on, sometime the image from a trapped particle became brighter and brighter, probably because additional nanotube particles agglomerated with the trapped particle, and the overall super-micron particle kept growing. Occasionally a trapped particle was knocked away by a newly arriving particle, which either got trapped or moved away from the trapping region. Sometimes the trapped particle has a small-amplitude oscillation and moves within a distance far smaller than the observed particle dimension. The trapped particle eventually reached a stable balance with less or no observable oscillation. It could become very still when the airflow was turned off, and/or when the cover laser sheet "lid" was on to keep the coming particles out. Also, Johnson grass smut spores (6.2-8.9 μm in diameter) can be trapped and released with a high trapping rate. FIG. 8 is a photographic illustration of a preferred embodiment chamber assembly separated in to three components. A selection of elements from the preferred embodiment of FIG. 1A are pictured in FIG. 8. The descriptions of the elements are incorporated by reference as though fully rewritten herein, wherein like numbers refer to like elements. The bottom subassembly is shown to the left, the middle subassembly is in the middle of FIG. 8 and the top subassembly is shown to the right. The bottom subassembly comprises the third passage or nozzle 63 and an elliptical mirror 36. The lateral faces of the chamber 35 are pictured centrally; optionally comprising four windows 34. The subassembly pictured to the right inserts into the top of the chamber 35 and the subassembly to the left inserts into the bottom of chamber 35 as readily appreciated by those skilled in the air. The subassembly on the right comprises a first passage (not discernible in the photograph) or nozzle 59 and second coaxial passage or nozzle 61. The upper portion comprises second chamber 60 having outlet 62. Also pictured is the inlet or cylinder 59.

Advantages

In accordance with the principles of the present invention, an improved on-line instrument is developed for detecting and characterizing aerosols, particularly a real-time device for detecting aerosolized biological, chemical threats using more informative optical signatures such as Raman spectra with big reduction of false positive alarm rate. The present invention significantly changes the current feeding methods for trapping particles in air, and is useful in various on-line analytical applications, in which long-time monitoring or analyzing from a series of successive arriving particles (e.g. different kind of individual particles from atmosphere, pharmaceutical or other production facilities) is required, but each of them needs to be trapped for a short time (e.g. a few seconds) observation or measurement.

Raman Signals and Capturing

The preferred embodiments of FIG. 1A, 1C, 3 may be utilized as a transportable system for studying bioaerosols (including aerosolized bioagents) and the effects of the atmosphere and sunlight on these, and for rapidly detecting and characterizing aerosolized chem- and bio-agents. It is also desirable to use Raman characterization technology to study the effects of the atmospheric environment (sunlight, humidity, & gasses such as ozone) on bioaerosols. The Raman scattering intensity $I_{fi}$ may be computed as:

$$I_{fi}(\pi/2) = \frac{\pi^2}{\varepsilon_0^2}(\tilde{v}_0 - \tilde{v}_{fi})^3 \tilde{v}_0 g_0 \sum_{\rho,o} [\alpha_{\rho\sigma}]_{ji} [\alpha_{\rho\sigma}]^*_{ji}$$

Where $$[\alpha_{\rho o}]_{fi} = \frac{1}{hc} \sum_{r \neq i,f} \left\{ \frac{[\mu_\rho]_{fr}[\mu_o]_{ri}}{\tilde{v}_{ri} - \tilde{v}_0 - i\Gamma_r} + \frac{[\mu_o]_{fr}[\mu_\rho]_{ri}}{\tilde{v}_{rf} + \tilde{v}_0 + i\Gamma_r} \right\}$$

power of the laser frequency. When the laser frequency is close to that of an electronic transition, it results in a huge absorption resonance effect. Most biological and chemical agents have high absorption at deep UV wavelengths. The high absorption will supply strong photophoretic forces for trapping Raman signals will increase by (frequency) and by resonant absorption. Raman spectra will avoid fluorescence interference of biological agents at wavelengths below 280 nm. The preferred methodology operates to draw particles into the trap at a sufficient rate to allow useful sampling rates, while also slowing the particles in the trapping volume so they can be trapped. However, different size/mass particles accelerate differently by drag force, the nozzle design is optimized. In addition, the best experimental conditions are developed to allow all particles in a certain size range (e.g., 2-20 mm) to be delivered to the small trapping volume and become trapped.

A hollow beam operates to trap absorbing or weakly-absorbing particles using photophoretic forces, and a tightly focused beam (green) to trap non-absorbing particles with radiation-pressure forces. The preferred embodiment system optionally measures Raman spectra of individual particles sampled from air (background or generated by the experimental set-up), and operates continuously in a sample-trap-measure-release mode. Since single-particle Raman signals are weak, the particles must be trapped; i.e., there is a need to draw and focus particles into the trap at sufficient sampling rates, while moving the particles slowly enough to reduce the drag force so they can be trapped. Electric field related traps require charging particles, which makes the setup complicated.

As generally known, Raman spectroscopy is a spectroscopic technique used to observe vibrational, rotational, and/or other low-frequency modes in a system; relying on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system. Typically, a sample is illuminated with a laser beam. Light from the illuminated spot is collected with a lens and sent through a monochromator. Wavelengths close to the laser line due to elastic Rayleigh scattering are filtered out while the rest of the collected light is dispersed onto a detector.

The present invention can aerodynamically focus, concentrate, and also slow the particles down using such a counter-flow coaxial-double-nozzle design. The present invention can feed aerosol particles to the very localized trapping region at an extremely low speed. The hollow cone surrounded by a conical high-intensity light surface provides a trap for absorbing or weakly-absorbing particles; while affording the capability of repeatedly trapping different successively arriving particles. The present invention offers the measurement of size and other properties of absorbing or weakly absorbing particles that do not need to be uniform. The present invention provides a device design that allows adequate optical windows 34 for optical observation and measurement. Optionally, the chamber 35 may be an air-tight chamber for sample manipulations, e.g., introduction of other chemical species into the chamber.

The present invention provides a novel integrated opto-aerodynamic system and demonstrates that it enables us to trap absorbing airborne micron-size particles from air, hold them and then release them, and to repeat this sequence many times as would be appropriate for continuous sampling of particles from air. The preferred embodiment shown in FIG. 1A comprises a conical photophoretic optical trap and a counter-flow coaxial-double-nozzle 59, 61 that focuses, concentrates and then slows particles for trapping. This technology should be useful for on-line applications that require monitoring (by single particle analyses) of a series of successively arriving particles (e.g., from the atmosphere or pharmaceutical or other production facilities) where the total sampling time may last from minutes to days, but where each particle must be held for a short time for measurements (e.g., Raman scattering). The aerodynamic design for delivering aerosol particles into a trapping region by the co-axis counter-flow double nozzle, which can concentrate and focus aerosol particles, and eventually deliver to a small trapping region at very slow speed, also can be used for any other trapping methods, such as using optical-pressure force, optical gradient force, electric, magnetic force, acoustic force.

As used herein the terminology "CCD" means charge coupled device.

As used herein the terminology "pump" means a device that raises, transfers, delivers, or compresses fluids or that attenuates gases especially by suction or pressure or both.

As used herein the terminology "outlet" means passage for escape or exit; a vent, an opening or passage by which anything is let out.

As used herein, the terminology "clean air flow" means a gaseous flow absent any particles.

As used herein the terminology "hollow beam" means a light beam, such as a laser beam, that look like a ring in cross-section.

Obviously, many modifications and variations of the present invention are possible in light of the above teachings. It is therefore to be understood that, within the scope of the appended claims, the invention many be practiced otherwise than as specifically described.

What is claimed is:

1. A system for trapping particles in a gaseous environment comprising:
- a chamber;
- an intake for intake of a gas into the chamber containing at least one particle to be trapped and released,
- an outlet for exit of the gas out of the chamber containing at least one particle;
- a first passage operatively connected to the intake operating to create a flow of a gas containing at least one particle into the chamber;
- a second passage operatively connected to the outlet for flow of the gas containing at least one particle from the chamber;
- a third passage operatively connected to a gaseous flow for creating a flow of fluid in a direction substantially opposite to the transfer of gas from the first passage so as to counteract or balance the flow of gas from the first passage;
- an image sensor for recording an image of the at least one particle;
- a laser for generating a light beam for forming a photophoretic trap located between the first and third passages;
- whereby due to the balance of forces of gases from the first and third passages and the photophoretic trap, a particle is suspended for viewing by the image sensor.

2. The system of claim 1 further comprising:
- at least one beam splitter for splitting the light beam into first and second components;
- an elliptical mirror for reflecting the first component operatively connected to the at least one beam splitter;
- a concave mirror for focusing light reflected from the elliptical mirror to create a conical portion of a photophoretic optical trap within the chamber;
- at least one lens for focusing the second component so as to create a laser plate portion of the photophoretic optical trap within the chamber.

3. The system of claim 1 wherein the first and second passages form a coaxial double nozzle and wherein the third passage is operatively connected to a clean gaseous flow for creating a flow of fluid absent any particles.

4. The system of claim 3 wherein the coaxial double nozzle has an inner nozzle connected to the intake and an outer nozzle connected to the exhaust, wherein gaseous fluid containing the at least one particle enters through the intake into the inner nozzle and into the photophoretic trap and wherein gaseous fluid containing the at least one particle exits the photophoretic trap through the outer nozzle.

5. A system for trapping particles in a gaseous environment comprising:

a laser for generating a beam of light;

at least one beam splitter for splitting the light beam into first and second components;

a chamber;

an elliptical mirror for reflecting the first component operatively connected to the at least one beam splitter;

a concave mirror for focusing light reflected from the elliptical mirror to create a conical portion of a photophoretic optical trap within the chamber;

at least one lens for focusing the second component so as to create a laser plate portion of the photophoretic optical trap within the chamber;

an intake for intake of a gas into the chamber containing at least one particle to be trapped and an outlet for exit of the gas out of the chamber containing at least one particle;

a first passage operatively connected to the intake operating to create a flow of a gas containing at least one particle into the chamber in the vicinity of the photophoretic trap;

a second passage operatively connected to the outlet for flow of the gas containing at least one particle from the chamber;

a third passage operatively connected to a clean gaseous flow for creating a flow of fluid in a direction substantially opposite to the transfer of gas from the first passage so as to counteract or balance the flow of gas from the first passage;

an image sensor for recording an image of the at least one particle;

whereby due to the balance of flow of gases from the first and third passages and the photophoretic trap, the at least one particle is suspended for viewing by the image sensor.

6. The system of claim 5 wherein the first and second passages form a coaxial double nozzle.

7. The system of claim 6 wherein the coaxial double nozzle has an inner nozzle connected to the intake and an outer nozzle connected to an exhaust, wherein gaseous fluid containing the at least one particle enters through the intake into the inner nozzle and into the photophoretic trap and wherein gaseous fluid containing the at least one particle exits the photophoretic trap through the outer nozzle.

8. The system of claim 5 further comprising a pair of axicon lenses and wherein the first light component passes though the pair of axicon lenses which produces a hollow beam that is reflected by the elliptical mirror and propagates up to the concave mirror to form the conical portion of a photophoretic optical trap within the chamber.

9. The system of claim 8 wherein the hollow beam operates to trap absorbing particles using photophoretic forces, and the second component comprises a tightly focused beam that operates to trap non-absorbing particles with radiation-pressure forces.

10. A system for trapping particles in a gaseous fluid comprising:

an intake for inputting gaseous fluid containing at least one particle;

a first pump operatively associated with the intake;

a chamber;

a first passage positioned within the chamber for flow of gaseous fluid containing at least one particle into the chamber;

a second passage coaxially positioned relative to the first passage for transfer of fluid containing at least one particle from the chamber;

a second pump operatively associated with the second passage for transfer of the gaseous fluid containing at least one particle from the chamber;

a third passage for flow of gaseous fluid in a direction opposite to the flow from the first passage which is configured to counteract or balance the flow of gaseous fluid from the first passage;

a viewer for viewing particles with the chamber, the particles entering the chamber by the first passage and exiting by the second nozzle passage, the first and third passages being positioned such that, due to the counteracting or balancing of forces of the gaseous fluids from said passages, the at least one particle is substantially stopped or suspended for viewing.

11. The system of claim 10 wherein the flow of gaseous fluid from the third passage is clean gaseous fluid and wherein the particles entering from the first passage are slowed by the interaction between the gaseous fluid from the third passage and the gaseous flow from the first passage so as to be effected by photophoretic forces.

12. The system of claim 10 wherein the viewer is a transparent window.

13. The system of claim 10 wherein the viewer is one of a spectrograph or a charge coupled device.

14. The system of claim 10 further comprising a laser for generating a beam of light;

at least one beam splitter for splitting the light beam into first and second light components;

an elliptical mirror for reflecting the first light component operatively connected to the at least one beam splitter;

a concave mirror for focusing light reflected from the elliptical mirror to create a conical portion of a photophoretic optical trap within the chamber located between the first and third passages;

at least one lens for focusing the second light component so as to create a blocking laser plate portion of the photophoretic optical trap;

whereby particles are confined within the photophoretic optical trap for viewing of particles by the viewer.

15. The system of claim 14 wherein the particles are slowed enough by the offsetting flows from the first and third passages so as to be trapped by photophoretic forces that are able to balance the small drag and gravitational forces.

16. The system of claim 15 wherein particles may be viewed in sequence by blocking and unblocking the trapping laser beam that forms the laser plate portion.

17. The system of claim 14 further comprising a cylindric lens for forming a blocking laser plate portion of the photophoretic optical trap so as to cover the conical portion of the photophoretic optical trap using a high-intensity light wall on the open side of the conical portion.

18. The system of claim 10 wherein the first and second passages form a coaxial double nozzle.

19. The system of claim 18 further comprising an outlet for the flow of gaseous fluid from the chamber and wherein the coaxial double nozzle has an inner nozzle connected to the intake and an outer nozzle connected to the outlet, wherein gaseous fluid containing the at least one particle enters through the intake into the inner nozzle and into the photophoretic trap and wherein gaseous fluid containing the at least one particle exits the photophoretic trap through the outer nozzle to the outlet.

20. The system of claim 10 wherein the at least one particle is one of anthax or bacteria.

* * * * *